United States Patent [19]

Loge et al.

[11] 4,184,256
[45] Jan. 22, 1980

[54] MINIATURE MOTOR HAVING AN INTERNAL COOLANT LINE

[75] Inventors: Hans Loge; Gerd Löhn, both of Biberach an der Riss, Fed. Rep. of Germany

[73] Assignee: Kaltenbach & Voigt GmbH & Co., Biberach an der Riss, Fed. Rep. of Germany

[21] Appl. No.: 859,952

[22] Filed: Dec. 12, 1977

[51] Int. Cl.² .............................................. A61C 1/08
[52] U.S. Cl. ................................... 433/82; 433/104
[58] Field of Search .............................. 32/28, 27, 26

[56] References Cited

U.S. PATENT DOCUMENTS

| | | | |
|---|---|---|---|
| 3,425,124 | 2/1969 | Hoffmeister | 32/28 |
| 4,007,529 | 2/1977 | Fleer | 32/27 |
| 4,080,737 | 3/1978 | Fleer | 32/27 |

Primary Examiner—Robert Peshock
Attorney, Agent, or Firm—Haseltine, Lake & Waters

[57] ABSTRACT

A miniature motor for driving a hand-held instrument such as a dental handpiece, the motor having at one end a connecting member for supplying coolant to a motor coolant line and motive energy to the motor, and at the other end a coupling member to which a hand-held instrument can be releasably connected. An intermediate coolant line in the coupling member serves to transfer coolant from the motor coolant line to a coolant supply line in the instrument which directs the coolant to a working implement at one end of the instrument. The coolant line in the motor comprises a tubular member which is removably mounted in the motor and has a releasable connection at its inlet end to a coolant supply connector in the connecting member, and a releasable connection at its outlet end to the intermediate coolant line in the coupling member. At least one of these releasable connections is provided in a closure member which is removable in order to render the tubular member accessible for servicing.

12 Claims, 6 Drawing Figures

MINIATURE MOTOR HAVING AN INTERNAL COOLANT LINE

This invention relates to a miniature motor having an internally located coolant line extending through the motor from one end of the motor to the other end of the motor, and having a connecting member arranged at said one end of the motor and provided with connecting elements for the supply of coolant to the inlet end of the coolant line and of motive energy to the motor, and also having a coupling member arranged at said other end of the motor and receiving the end of a drive shaft projecting from the motor, the said coupling member being provided with coupling elements for releasably connecting a hand-held instrument to the motor, the instrument having a drive shaft adapted to be coupled with the end of the motor drive shaft and also a coolant supply line adapted to be connected with the outlet end of the coolant line of the motor and extending to a working implement connected to the instrument.

The hand-held instrument may be a surgical, in particular a dental handpiece, with which arrangement the implement driven by the drive shaft may be a drill, a grinding implement or the like. The miniature motor is preferably an electric motor, with which arrangement the coolant flowing through the coolant line, for example water or a spray consisting of an air-water mixture, can be employed not only for cooling the implement or the workpiece, for example a live tooth, but also for cooling the motor. In this case, the coolant is heated by the operating warmth of the motor during throughflow through the coolant line, so that in the case of a dental handpiece it emerges out of the coolant supply line and impinges on the tooth to be treated in a manner which is pleasant for the patient, for example approximately at body temperature; the miniature motor may, however, also be constituted by an air motor. The arrangement of the coolant line in the interior of the motor has, relative to motors having externally located coolant lines, the advantage that the user of the instrument is not hindered by the coolant line.

In the case of the known miniature motors of this type, the outlet end of the coolant line projects in the form of a nipple out of the end face of the motor into the open air. This nipple serves for releasable connection with the coolant supply line of the hand-held instrument, designed as a flexible hose, the said coolant supply line extending externally along the instrument to the implement. Due to calcination of the coolant, for example water, especially when it is heated, or due to other contaminants, there may be clogging in the coolant line which usually has a small diameter of approximately 0.5 to 1 mm, for example 0.7 mm, arranged in the interior of the motor. Cleaning or replacement of the clogged coolant line in the known motors is impossible without complete disassembly of the motor, since the coolant line is secured in the motor and its inlet end is not accessible. Disassembly of the motor is inconvenient and costly, especially since for this purpose the motor must be sent away for repair by the user.

It is an object of the invention to provide a miniature motor of the type mentioned at the outset wherein cleaning and possible replacement of the coolant line arranged in the interior of the motor is possible in simple manner without dismantling the motor.

According to the invention there is provided a miniature motor for driving a hand-held instrument and comprising:

a coolant line provided internally of the motor and extending generally axially of the motor from one end of the motor to the other end of the motor, the coolant line having an inlet and an outlet located near said one end and said other end of the motor respectively;

a connecting member arranged at said one end of the motor;

first and second connector elements provided by said connecting member for the supply of coolant and motive energy respectively to the motor, the first connector element being connected to said inlet of the coolant line;

a coupling member arranged at said other end of the motor;

releasable connecting means enabling the releasable connection of a hand-held instrument to the coupling member, the instrument having a drive shaft for driving a tool connected to the instrument and a coolant supply line connectible to said coolant line and extending towards said tool;

a motor shaft projecting from said other end of the motor and connectible drivingly to said drive shaft when the instrument is connected to said coupling member;

and an intermediate coolant line provided in said coupling member and having an outlet connectible to said coolant supply line of the instrument when the latter is connected to the coupling member;

in which the coolant line in said motor comprises a tubular member which is removably mounted in said motor and which has a releasable connection at its inlet end with said first connector element and a releasable connection at its outlet end with said intermediate coolant line;

and at least one of said releasable connections is provided in a closure element which is removable in order to render said tubular member accessible.

If desired, a plurality of tubular members may be provided, in which case these may be arranged in juxtaposition or concentrically one within the other in the interior of the motor. In the case of an arrangement of two tubular members, by way of example one of the tubular members may serve for the passing-through of cooling water and the other tubular member for the passing-through of cooling air, these two coolants optionally being mixed for example in the zone of their outflow out of the coolant supply line in the vicinity of the implement, to constitute a spray emerging in the zone of the implement. If exchange of heat between the coolant flowing through the tubular member and the tubular member itself or in particular the environment of the tubular member is to be avoided, the tubular member is expediently made from heat-insulating material or it is layered with heat-insulating material. The closure member can be constituted by the connecting member or (as will be discussed later) by the coupling member.

The design proposed affords the advantage that after release of the closure element, the latter can be removed from the motor in simple manner, preferably in the direction parallel to the tubular member extending through the motor. As this is done, simultaneously at least one of the two releasable connections, e.g. plug-in connections, is released, so that during removal of the closure element (when the plug-in connection at the inlet end is released) simultaneously the tubular member is pulled-out of the motor. The tubular member can then be cleaned from its inlet end, for example by pushing-through by means of a wire, or can be replaced by a fresh tubular member. If, on removing the closure member the plug-in connection at the outlet end, or both plug-in connections, become released, the tubular member may after removal of the closure member be pulled out of the motor and then also cleaned or replaced. Installation of the tubular member in the motor is effected in the reverse sequence. These manipulations can be effected in simple manner by the user himself, for example by a dentist or an assistant (when the hand-held instrument is a dental handpiece), without dismantling the motor. In this way, if the coolant line is clogged, it becomes unnecessary to send the motor to a repair shop.

Restoration of the plug-in connection at the inlet end on fitting the tubular member in the motor can be effected especially simply if the (first) coolant connector element is designed as a pipe stub or nipple pointing into a recess formed between the connecting member and the motor; in this recess, apart from the pipe stub, the plug-in connection and the inlet end of the pipe stub projecting from said one end of the motor are arranged and covered by a wall or housing portion of the motor which projects in sleeve-like manner and extends as far as the connecting member.

Thereby, it is guaranteed that the tubular member, on restoring the plug-in connection at the inlet end, can readily be pushed on to the pipe stub.

The coolant connector element may be provided at a coolant regulating device arranged in the motor or preferably, expediently releasably, in the connecting member.

If the plug-in connections are not effected by automatically and sealingly pushing one within the other, the two ends of the tubular member and the mouth of the coolant connector element or the inlet end of the intermediate coolant line, then the plug-in connection may be provided in each particular instance with a packing.

The packing may be constituted by a sealing ring, preferably an O-ring, the latter facilitating threading-in of the tubular member due to the tapering passage-mouth formed in consequence of the circular cross-section, in particular on restoring the plug-in connection at the inlet end.

A preferred embodiment has the coolant connector element formed by a dispensing bore of a coolant regulating device having a larger cross-section than the tubular member, there being arranged in the dispensing bore a sealing ring which embraces the inserted inlet end of the tubular member.

The packing may also in each particular instance be formed by a flexible connecting hose pushed over or into the ends of the tubular member and the mouth of the coolant connector element or the inlet end of the intermediate coolant line of the coupling member. In particular in this case, threading-out and in of the tube or line ends to be separated or connected, on effecting extraction and insertion of the tubular member, can be facilitated by the arrangement whereby the packing arranged in the zone of the connecting member is secured against longitudinal displacement in both directions and the packing arranged in the zone of the coupling member is secured against longitudinal displacement at least in the direction of the connecting member.

Expediently, the tubular member is arranged in at least one receiving duct formed in the interior of the motor. The receiving duct makes possible further facilitation of threading-in of the tubular member on installing the latter in the motor.

In a further preferred embodiment the closure element is constituted by the coupling member and the tubular member extends externally of the rotor of the motor, substantially parallel to the motor shaft, and is bent over at its outlet end at an obtuse angle, to extend towards a coupling sleeve of the coupling member which has a smaller cross-section than the motor, surrounds the drive end of the motor shaft and receives in its wall the intermediate coolant line, the intermediate line being bent over in the zone of its inlet end to correspond to the bent-over portion of the tubular member. This embodiment has the advantage that, on removing the coupling member, simultaneously the tubular member (releasably connected due to the plug-in connection with the bent-over inlet end of the intermediate line) is automatically also drawn out of the motor whilst withdrawing from the plug-in connection at its inlet end. Thereupon, the tubular member can, if so desired, readily be drawn-off from the plug-in connection and cleaned or replaced by a fresh tubular member.

In this respect, it is expedient if the bent-over inlet end of the intermediate coolant line projects from the coupling member and is, like the plug-in connection and the outlet end of the tubular member projecting from the motor, arranged in a recess formed between the motor and the coupling member and covered over by a wall or housing element of the coupling member projecting in sleeve-like manner and extending as far as the motor.

The previously mentioned removal of the coupling member becomes unnecessary if the closure member is constituted by an insert member secured to the outlet end of the tubular member and releasably inserted from the exterior into a passage formed in the coupling member, the said insert member having an outlet duct connected with the outlet end of the tubular member and which is connected with the intermediate coolant line of the coupling member. According to this embodiment, on releasing and removing the insert member, simultaneously, accompanied by release of the plug-in connection at the inlet end, the tubular member is pulled-out of the motor without the coupling member itself requiring to be removed.

In order that, on re-inserting the insert member, it shall be unnecessary to pay attention to corresponding position of the mouth of the outlet duct and the mouth of the intermediate coolant line, it is proposed that the outlet duct of the insert member shall be connected via an external annular duct of the insert member with the intermediate coolant line. For facilitating in particular the extraction of the insert member out of the passage in the coupling member, the insert member may be provided with spanner or other tool engagement means. Expediently, the insert member is sealed relative to the passage in the coupling member by means of packings arranged on both sides of the outlet duct. With this arrangement, the elasticity of the sealing rings makes it possible to plug the insert member to be jammed fast in stopper-like fashion in the passage of the coupling member. The insert member can, however, also be screwed into the passageway in the coupling member.

DESCRIPTION OF THE PREFERRED EMBODIMENTS

Figure 1:
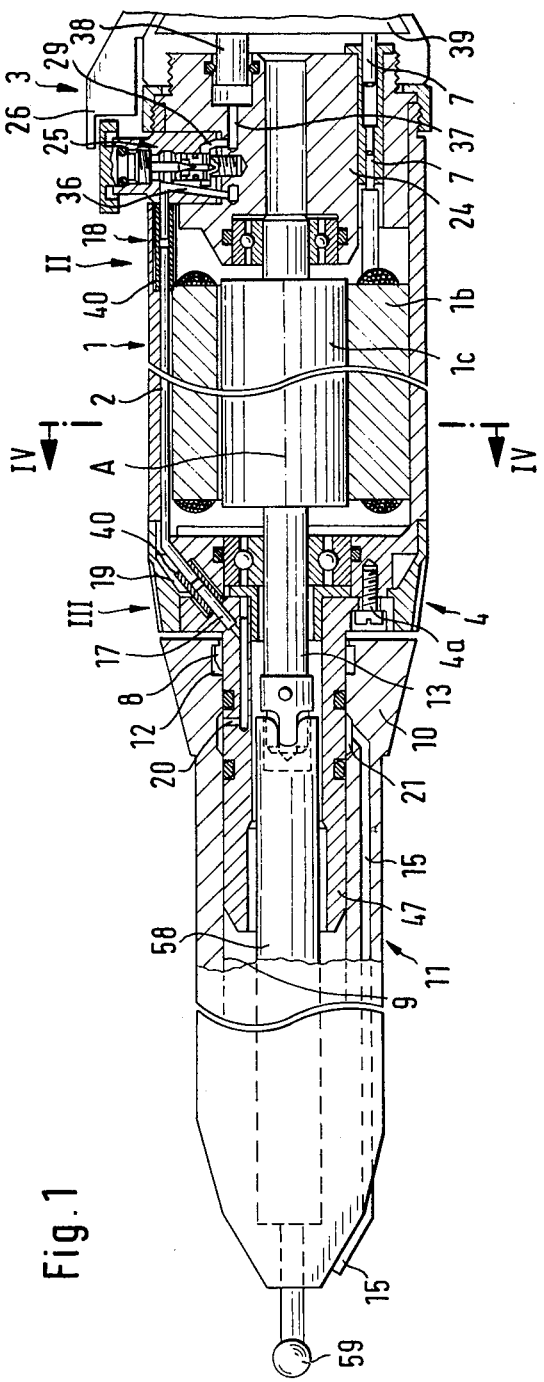
FIG. 1 is a longitudinal sectional view of a miniature motor with a connecting member at one end and a coupling member at the other end.

The miniature motor 1 shown has a coolant line arranged in its interior and constituted by a tubular member 2. The member 2 extends through the motor 1, designed as an elongage cylinder, from one end of the motor to the other end. The motor 1 is provided at one end with a connecting member 3 and at the other end with a coupling member 4. The connecting member 3 has first connecting elements 5 (FIGS. 2 and 5) for feeding coolant to the inlet end 6 of the member 2, and second connecting elements 7 for supplying motive energy to the motor 1. In the case illustrated, the miniature motor 1 is an electric motor, for which reason the connecting elements 7 comprise an electrical plug-in connection. When the motor 1 is pneumatically operated, the connecting elements 7 will comprise means for supplying compressed air to the motor.

The coupling member 4 has coupling elements in the form of a per se known resilient hooks 8 (FIG. 1) engaging in an annular groove 12 arranged in the inner wall 9 of the open, sleeve-like end 10 of a handpiece-like instrument 11. Thereby, pivotability is achieved of the instrument 11 relative to the coupling member 4, and relative to the motor 1, the latter being connected for example by means of three screws 4a with the coupling member 4.

The coupling member 4 receives the drive end 13 of a motor shaft projecting from the motor 1. The elements 8, 12 serve for releasable connection of the instrument 11 to the motor 1. The instrument 11 has a drive shaft 58 adapted to be coupled with the drive end 13 of the motor shaft, for driving an implement 59 connected to the end of the drive shaft 58 remote from the drive end 13, and the instrument 11 also has a coolant supply line 15 extending to the implement 59 and adapted to be connected with an outlet end 14 (FIGS. 3 and 6) of the tubular member 2.

The member 2 is releasably connected at its inlet end 6 to the coolant connecting element 5 of the connecting member 3 and at its outlet end 14 to the inlet end 16 of an intermediate coolant line 17 provided in the coupling member 4 and adapted to be connected to the coolant supply line 15 of the instrument 11. The connections at each end of member 2 are effected releasably by respective plug-in connections 18, 19. The intermediate coolant line 17 in the coupling member 4 has a radial outlet duct 20 which opens into an inner annular duct 21 of the instrument 11. The coolant supply line 15 extends from this annular duct 21. As apparent from FIG. 6, there is formed in the coupling member 4 also a further coolant intermediate line 17' having a radial outlet duct 20', provided in cases wherein (not apparent from FIG. 6) a further coolant line constituted by a tubular member is provided in the miniature motor 1.

Figure 3:
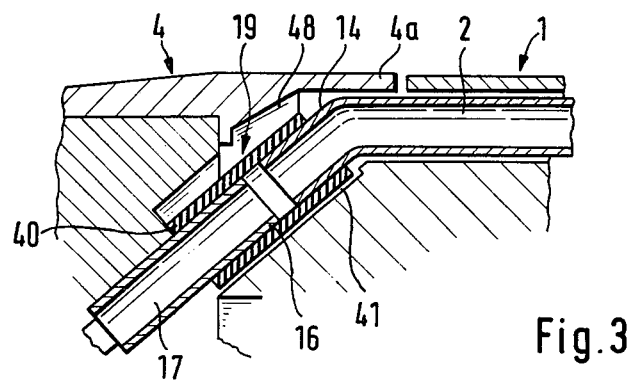
FIG. 3 shows the detail III of FIG. 1, drawn to a larger scale.
Figure 6:
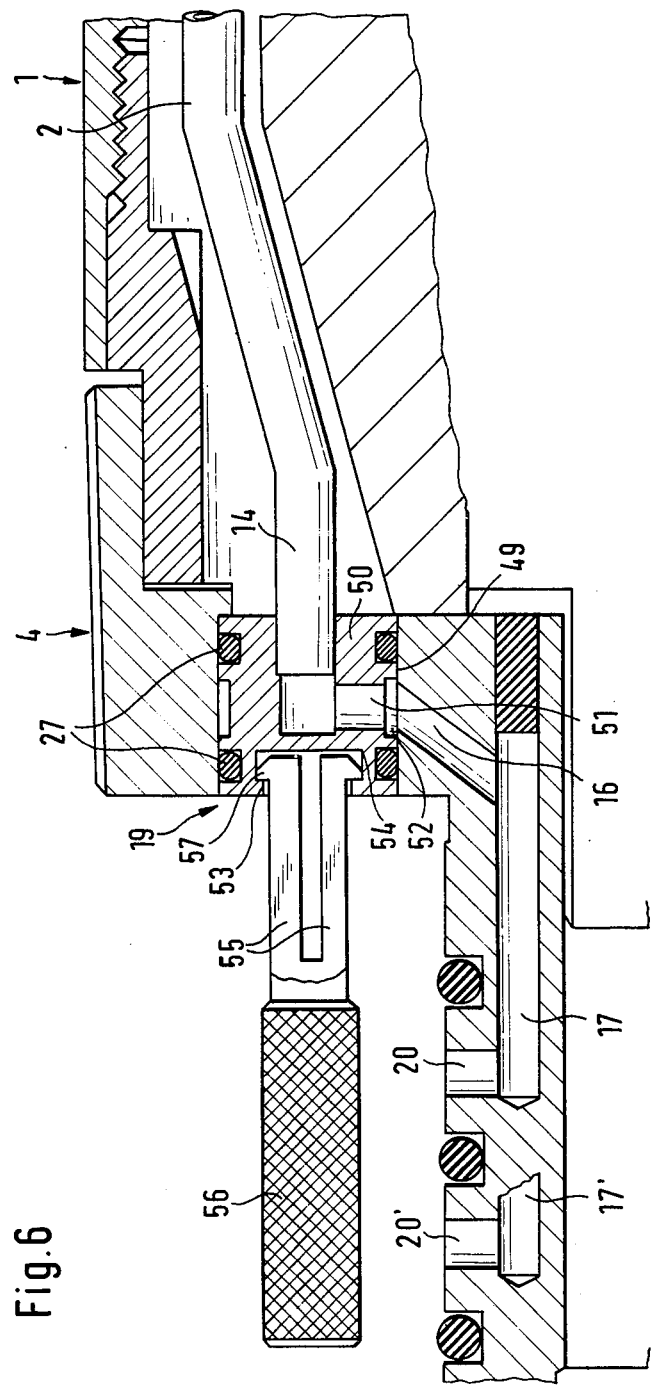
FIG. 6 is a view, similar to FIG. 3, of a further embodiment.

The plug-in connection 19 is, according to FIGS. 1, 3 and 6, arranged in a closure element removable in the general direction of the tubular member 2, i.e. in the direction of the motor axis A and, after removal, rendering the tube member accessible. In the case of the embodiments according to FIGS. 1 and 3, the closure element is constituted by the coupling member 4.

Figure 2:
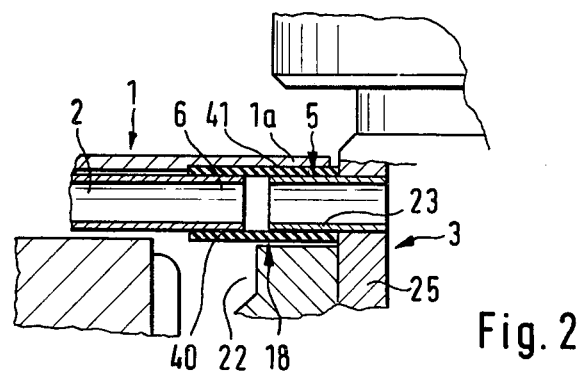
FIG. 2 shows the detail II of FIG. 1, drawn to a larger scale.

The connecting element 5 is, in the case of the embodiment according to FIG. 2, designed as a pipe stub 23 facing into a recess 22 formed between the connecting member 3 and the motor 1. There are arranged in the recess 22, apart from the pipe stub 23, the plug-in connection 18 and the inlet end 6 of the tubular member 2, the latter projecting from one end of the motor end. These elements are covered by a wall element 1a of the motor 1 which projects in sleeve-like manner and extends as far as the connecting member 3.

Provided at the inner body 24 of the connecting member 3 is a coolant regulating device 25. After releasing the plug-in connection 18 and after removal of a clamping nut 26 (as shown in FIG. 1) which partially covers the coolant regulating device 25, the coolant regulating device can in case of need be removed. As apparent from FIGS. 1, 2 and 5, the coolant connecting element 5 is provided at the coolant regulating device 25.

Figure 5:
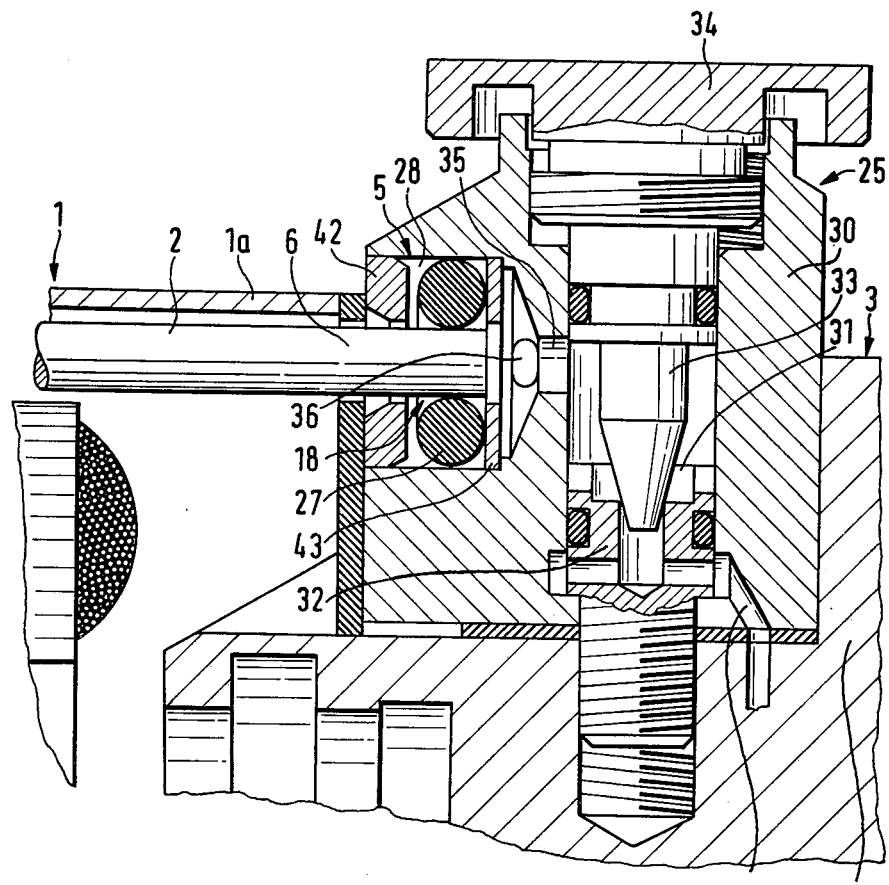
FIG. 5 is a view, similar to FIG. 2 of an alternative embodiment.

Each plug-in connection 18, 19 is provided with a respective packing. Referring to FIGS. 5 and 6, the packings are each constituted by a sealing ring 27. Referring to FIG. 5, the packing ring 27 is an O-ring.

Furthermore, in the case of the embodiment according to FIG. 5, the connecting element 5 is constituted by a coolant dispensing bore 28 of the coolant regulating device 25, which has a larger cross-section than the tubular member 2. Arranged in the coolant dispensing bore 28 is the sealing ring 27 which embraces the inserted inlet end 6 of the tubular member 2.

Referring to FIG. 5, the coolant regulating device 25 has an inlet duct 29 which extends through a valve housing 30 and opens into an inner valve chamber 31. Provided in the chamber 31 is a valve seat 32 for a valve body 33 which, by means of a screwable rotating grasping means 34, can be lifted-off from the valve seat 32 and again lowered on to it. From the inner chamber 31, an outlet duct 35 opens into the coolant dispensing bore 28. Into the dispensing bore 28 there opens also (according to FIGS. 1 and 5) an air line 36, so that an air-water mixture can be formed in the dispensing bore 28. As apparent from FIG. 1, the inlet duct 29 is connected to a supply duct 37 which is connected to a plug-in tube 38 of a plug-in member 39 connected upstream of the connecting member 3.

In the case of the embodiments according to FIGS. 1 to 3, the packing for each plug-in connection 18, 19 is constituted by a flexible connecting hose 40. The connecting hose 40 at the inlet end of member 2 is pushed over the ends of the tubular member 2 and also over the pipe stub 23 constituting the coolant connecting element 5, and at the outlet end is pushed over end 14 and over the inlet end 16 of the intermediate coolant line 17.

Referring to FIGS. 1 to 5, the packing arranged in the zone of the connecting member 3 is secured against longitudinal displacement in both directions and the packing arranged in the zone of the coupling member 4 is also secured against longitudinal displacement. For this purpose, according to FIGS. 2 and 3, the connecting hose 40 is arranged in a recess 41 in the walls 1a of the motor and in the connecting member 3 (FIG. 2) or in the coupling member 4 (FIG. 3). In the case of the embodiment according to FIG. 5, for the same purpose of the packing ring 27 is secured by a counter-ring 42 inserted in the dispensing bore 28 and by an intermediate ring 43 bearing against the end of the dispensing bore 28.

Figure 4:
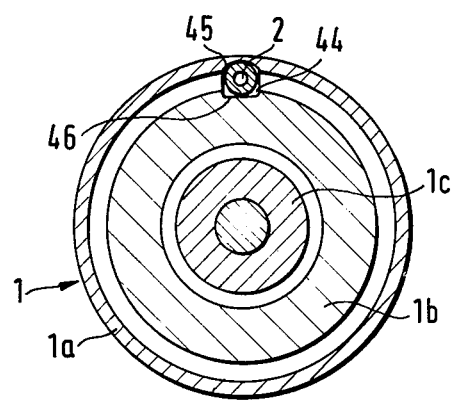
FIG. 4 is a section taken along the line IV—IV in FIG. 1.

As apparent from FIG. 4, the tubular member 2 is provided in a receiving duct 44 arranged in the interior of the motor 1. For this purpose, the walls 1a of the motor 1 have at the inner side of the stator 1b of the motor 1 in each particular instance a groove-formed recess 45, 46. The two groove-form recesses 45, 46 face each other.

In the case of the embodiment according to FIGS. 1 to 3, (according to which the closure element is constituted by the coupling element 4), the tubular member 2 extends externally of the rotor 1c and substantially parallel to the axis A of the motor 1, i.e. to the motor shaft. At its end adjacent the coupling-member 4, i.e. in the zone of the outlet end 14, the tubular member 2 is bent over at an obtuse angle and is directed towards the inlet end 16 of the intermediate coolant line 17. The line 17 is arranged in a coupling sleeve 47 of the coupling member 4 which has a smaller cross-section than the motor 1 and surrounds the drive end 13 of the motor shaft. The intermediate line 17 is, in the zone of its inlet end 16, also bent over to correspond to the bent-over portion of the tubular member 2. The inlet end zone 16 of the intermediate line 17 projects from the coupling member 4 and is, like the plug-in connection 19 and the outlet end 14 of the tubular member 2, arranged in a recess 48 formed between motor 1 and coupling member 4 and covered by a wall element 4a of the coupling member 4, which wall element 4a projects in sleeve-like fashion and extends as far as the motor 1.

In the case of the embodiment according to FIG. 6, the closure element of plug-in connection 19 is constituted by an insert member 50 secured to the end of the tubular member 2 and inserted from the exterior into a passage 49 formed in the coupling member 4. The insert member 50 has an outlet duct 51 connected with the outlet end 14 of the tubular member 2 and which is connected to the intermediate coolant line 17 of the coupling member 4. The outlet duct 51 is connected via an outer annular duct 52 of the insert member 50 to the intermediate line 17 of the coupling member 4. The insert member 50 is furthermore provided with tool engagement means 53 constituted by a bore having a widened portion 54 which is T-shaped in section. Into this widened portion 54 there engage the hooked ends 57 of resilient tongues 55 of a key or spanner 56. After insertion of the hooked ends 57 (which spread-apart following entry into widened portion 54), the insert member 50 can be extracted from the passage 49.

As FIG. 6 also shows, the insert member 50 is sealed relative to the passage 49 (formed in the coupling member 4) in that in each particular instance a sealed ring 27 is arranged at both sides of the outlet duct 51 and of the annular duct 52.

The insert member can be clamped in stopper-like fashion into the passage 49 formed in the coupling member 4; however, it is also possible that it may be screwed into the passage 49.

We claim:

1. A miniature motor for driving a hand-held instrument, comprising: an internal coolant line extending from one end of the motor to the other end of the motor, said internal coolant line having an inlet and an outlet located near said one end and said other end, respectively; a connecting member having connector elements for supplying coolant to said inlet and energy to said motor; a coupling member arranged on said other end of said motor; a motor shaft projecting from said other end of said motor and having a driving end; said coupling member having coupling elements for detachable connection to a hand-held instrument having a driveshaft for driving a tool connected to said instrument; a coolant line leading to said tool and sealingly connectable to said outlet, said coolant line comprising at least one tubular member removably located in said motor; an intermediate coolant line; said tubular member having an entry end connected to one of said connector elements for supplying coolant and an exit end for detachably connecting to an entry end of said intermediate coolant line; plug-in connection means for connecting said intermediate coolant line to said coolant line; said plug-in connection means being arranged in a holder removable in the direction of said tubular member passing through said motor and providing access to said tubular member after removal; a flexible connecting tube slid over said entry end and said exit end of said tubular member and a discharge end of said connector element for supplying coolant and said entry end of said intermediate coolant line in said coupling member.

2. A miniature motor for driving a hand-held instrument, comprising: an internal coolant line extending from one end of the motor to the other end of the motor, said internal coolant line having an inlet and an outlet located near said one end and said other end, respectively; a connecting member having connector elements for supplying coolant to said inlet and energy to said motor; a coupling member arranged on said other end of said motor; a motor shaft projecting from said other end of said motor and having a driving end; said coupling member having coupling elements for detachable connection to a hand-held instrument having a driveshaft for driving a tool connected to said instrument; a coolant line leading to said tool and sealingly connectible to said outlet, said coolant line comprising at least one tubular member removably located in said motor; an intermediate coolant line; said tubular member having an entry end connected to one of said connector elements for supplying coolant and an exit end for detachably connecting to an entry end of said intermediate coolant line; plug-in connection means for connecting said intermediate coolant line to said coolant line; said plug-in connection means being arranged in a holder removable in the direction of said tubular member passing through said motor and providing access to said tubular member after removal; an exit duct leading to said intermediate coolant line; an insert member; a passage of said coupling member connected to said exit end of said tubular member; and a pair of packing rings for sealing said outlet duct in said insert member detachably inserted in said passage.

3. A miniature motor as defined in claim 1 wherein said connecting element for supplying coolant is a pipe stub pointing to a recess between said connecting member and said motor, said recess housing said plug-in connection and said entry end of said tubular member, said entry end projecting from said motor on the connecting member side, said plug connection and said entry end being covered by a sleeve-like projecting wall portion of said motor extending to said connecting member.

4. A miniature motor as defined in claim 1 including packing formed by said flexible connecting tube slid over said entry end and said exit end of said tubular member and a discharge end of said connector element for supplying coolant and said entry end of said intermediate coolant in said coupling member, said packing being arranged in the region of said connecting member and secured against longitudinal displacement in both directions, said packing being also arranged in the region of said coupling member and secured against longitudinal displacement at least in the direction of said connecting member.

5. A miniature motor as defined in claim 1 including at least one receiving duct inside said motor for locating said tubular member.

6. A miniature motor as defined in claim 1 including a holder comprising said coupling member; a rotor and a motor shaft, said tubular member extending outside said rotor and said motor parallel to said motor shaft, said tubular member being bent in the region of said exit end at an obtuse angle to extend towards a coupling sleeve of said coupling member, said coupling sleeve having a smaller cross section than said motor and enclosing a driving end of said motor shaft for receiving said intermediate coolant line in a wall of said coupling sleeve, said intermediate coolant line being arranged coaxially in the region of said entry end corresponding to the direction of said bent exit end of said tubular member.

7. A miniature motor as defined in claim 6 including an inlet end region of said intermediate coolant line, said inlet end region projecting from said coupling member and being arranged, jointly with said plug-in connection and said exit end, in a recess between said motor and said coupling member and being covered by a sleeve-like projecting wall portion of said coupling member extending to said motor.

8. A miniature motor as defined in claim 2 wherein said outlet duct of said insert member is connected to said intermediate coolant line of said coupling member via an annular duct of said insert member, said packing rings being arranged on both sides of said outlet duct and contacting said passage of said coupling member.

9. A miniature motor as defined in claim 2 wherein said insert member has tool engagement means.

10. A miniature motor as defined in claim 2 wherein said insert member is inserted with stooper-like clamping effect into said passage of said coupling member.

11. A miniature motor as defined in claim 2 wherein said insert member is screwed into said passage in said coupling member.

12. A miniature motor as defined in claim 1 including packing formed by said flexible connecting tube slid over said entry end and said exit end of said tubular member and a discharge end of said connector element for supplying coolant and said entry end of said intermediate coolant in said coupling member, said packing being arranged in the region of said connecting member and secured against longitudinal displacement in both directions, said packing being also arranged in the region of said coupling member and secured against longitudinal displacement at least in the direction of said connecting member; said connecting element for supplying coolant being a pipe stub pointing to a recess between said connecting member and said motor, said recess housing said plug-in connection and said entry end of said tubular member, said entry end projecting from said motor on the connecting member side, said plug connection and said entry end being covered by a sleeve-like projecting wall portion of said motor extending to said connecting member; at least one receiving duct inside said motor for locating said tubular member; a holder comprising said coupling member; a rotor and a motor shaft, said tubular member extending outside said rotor and said motor parallel to said motor shaft, said tubular member being bent in the region of said exit end at an obtuse angle to extend towards a coupling sleeve of said coupling member, said coupling sleeve having a smaller cross section than said motor and enclosing a driving end of said motor shaft for receiving said intermediate coolant line in a wall of said coupling sleeve, said intermediate coolant line being arranged coaxially in the region of said entry end corresponding to the direction of said bent exit end of said tubular member; an inlet end region of said intermediate coolant line, said inlet end region projecting from said coupling member and being arranged, jointly with said plug-in connection and said exit end, in a recess between said motor and said coupling member and being covered by a sleeve-like projecting wall portion of said coupling member extending to said motor.

* * * * *